United States Patent [19]

Stone

[11] Patent Number: 4,880,429
[45] Date of Patent: Nov. 14, 1989

[54] PROSTHETIC MENISCUS

[76] Inventor: Kevin R. Stone, 133 Retiro Way, San Francisco, Calif. 94123

[21] Appl. No.: 75,352

[22] Filed: Jul. 20, 1987

[51] Int. Cl.⁴ ............................................. A61F 2/30
[52] U.S. Cl. ...................................... 623/18; 623/20; 623/16; 128/DIG. 8; 530/356
[58] Field of Search .................... 128/1 R, DIG. 8; 530/356; 623/16, 18, 20

[56] References Cited

U.S. PATENT DOCUMENTS

| | | | |
|---|---|---|---|
| 3,443,261 | 5/1969 | Battista et al. | 623/16 |
| 3,551,560 | 12/1970 | Thiele | 623/16 X |
| 3,855,638 | 12/1974 | Pilliar | 623/16 |
| 4,055,862 | 11/1977 | Farling | 623/20 X |
| 4,060,081 | 11/1977 | Yannas et al. | 128/156 |
| 4,085,466 | 4/1978 | Goodfellow et al. | 3/1.91 |
| 4,280,954 | 7/1981 | Yannas et al. | 260/123.7 |
| 4,291,013 | 9/1981 | Wahlig et al. | 623/16 X |
| 4,344,193 | 8/1982 | Kenny | 623/20 |
| 4,350,629 | 9/1982 | Yannas et al. | 260/123.7 |
| 4,351,069 | 9/1982 | Ballintyn et al. | 623/16 X |
| 4,378,224 | 3/1983 | Nimni et al. | 8/94.11 |
| 4,385,404 | 5/1983 | Sully et al. | 623/18 |
| 4,400,833 | 8/1983 | Kurland | 623/20 X |
| 4,418,691 | 12/1983 | Yannas et al. | 128/156 |
| 4,448,718 | 5/1984 | Yannas et al. | 128/DIG. 8 X |
| 4,458,678 | 7/1984 | Yannas et al. | 128/155 |
| 4,472,840 | 9/1984 | Jefferies | 623/16 |
| 4,502,161 | 5/1985 | Wall | 3/1.91 |
| 4,505,266 | 3/1985 | Yannas et al. | 128/1 R |
| 4,542,539 | 9/1985 | Rowe, Jr. et al. | 623/16 |
| 4,544,516 | 10/1985 | Hughes et al. | 128/DIG. 8 X |
| 4,614,794 | 9/1986 | Easton et al. | 530/356 |
| 4,627,853 | 12/1986 | Campbell et al. | 623/16 |

FOREIGN PATENT DOCUMENTS

1170001 7/1984 Canada.
1515963 6/1978 United Kingdom.
8303536 10/1983 World Int. Prop. O..

OTHER PUBLICATIONS

Leenslag et al., (1986) *Biological and Biomechanical Performance of Biomaterials* (Christel et al., eds.) Elsevier Science Publishers B.V., Amsterdam, (1986), pp. 147–152.

*Primary Examiner*—Richard J. Apley
*Assistant Examiner*—David J. Bender
*Attorney, Agent, or Firm*—Lahive & Cockfield

[57] ABSTRACT

A prosthetic meniscus is disclosed which can be implanted in a humanoid knee, and which can act as a scaffold for regrowth of native meniscal tissues. The meniscus comprises a three dimensional array of collagen fibers interspersed with glycosaminoglycan molecules. The collagen fibers are present at a concentration of about 65 to 98 percent by dry weight, and the glycosaminoglycan molecules are present at a concentration of about 1 to 25 percent by dry weight. Cross-links are provided by at least a portion of the glycosaminoglycan molecules, and may consist of at least one of the group comprising chondroitan 4-sulfate, chondroitan 6-sulfate, keritan sulfate, dermatan sulfate, heparin sulfate, and hyaluronic acid.

12 Claims, 1 Drawing Sheet

PROSTHETIC MENISCUS

BACKGROUND OF THE DISCLOSURE

The present invention is in the field of implantable medical devices, and more particularly, is directed to devices useful as prosthetic menisci.

The meniscus acts in the knee joint as a crucial stabilizer, a mechanism for force distribution, and a lubricant in the area of contact between the tibia and femur. Without the meniscus, stress concentration occurs in the knee in conjunction with abnormal joint mechanics, and premature development of arthritic changes from collagen stress occurs.

In the prior art, treatment of injured or diseased menisci has generally been both by surgical repair and by excision. With excision, regeneration of meniscal tissue may occur. Additionally, it is known that meniscal fibrochondrocytes have the ability to migrate into a defect filled with a fibrin clot and form tissue apparently similar to normal meniscal fibrocartilage. When an adequate matrix scaffold is present within a meniscal defect, such meniscal fibrocartilage may be formed. Meniscal tissue is also capable of self-repair when exposed to bleeding tissues, and additionally, it is also known in the prior art that meniscal cells in tissue culture are capable of cell division and matrix synthesis. Replacement of an injured meniscus in an otherwise healthy joint may prevent arthritic changes and may stabilize the joint. In diseased joints, replacement of the meniscus may reduce the progression of the disease process, and may provide pain relief. Allografting or meniscal transplantation, is one method of replacement which has been executed both in dogs and in humans. However, this approach has been only partially successful over the long term due to the host's immunologic response to the graft, to failures in the cryopreservation process, and to failures of the attachment sites.

In alternative prior art replacement approaches, menisci have been replaced with prostheses composed of artificial materials. Such prostheses have been constructed of purely artificial materials in order to minimize the possibility of an immunological response. In addition, the use of such materials is believed to be advantageous because it permits construction of a structure which can withstand the high and repeated loads which are encountered in the knee joint, and because it can alter the joint mechanics in beneficial ways that biological materials would not tolerate. For example, a Teflon net has been used to replace the resected meniscus of a dog upon which fibrous ingrowth or regeneration was observed, although accompanied by significant chondral abrasion. A prosthetic meniscus has also been constructed from resilient materials such as silicone rubber or Teflon with reinforcing materials of stainless steel or nylon strands (U.S. Pat. No. 4,502,161). In addition, a meniscal component has been made from resilient plastic materials as disclosed in U.S. Pat. No. 4,085,466. Reconstruction of meniscal lesions have been attempted with carbon-fiber-polyurethane-poly (L-lactide) with minimal success.

Generally, the replacement of meniscal tissue with structures consisting of artificial materials has been unsuccessful, principally because the opposing articular cartilage of human and animal joints is fragile. The articular cartilage in the knee will not withstand abrasive interfaces, nor compliance variances from normal, which eventually results from the implantation of prior art artificial menisci. Additionally, joint forces are multiples of body weight which, in the case of the knee and hip, are typically encountered over a million cycles per year. Thus far, prior art artificial menisci have not been soft, durable, or lubricative enough, nor have they been able to be positioned securely enough to withstand such routine forces.

Prostheses, in general, have been devised out of at least some of the constituents of the structures which they are replacing, or out of materials not considered to be immunogenic to the body. For example, Yannas et al., fashioned endodermal implants, synthetic epidermis (U.S. Pat. No. 4,060,081), and sciatic nerve guides out of collagen and glycosaminoglycans, which are biochemical constituents of many body organs. By adjusting the pore size and axes of the pores and fibers comprising these structures, regrowth could be stimulated, and was, indeed, observed. Further regrowth has been advanced by seeding of the nerve guide with Schwann cells prior to implantation. However, even with the foregoing technologies which have been applied to the reconstruction of anatomical structures other than knee joints, a structure suitable as a prosthetic meniscus and constructed from natural materials has not been developed in the prior art.

Accordingly, it is an object of this invention to provide a meniscal replacement or prosthesis.

Another object is to provide a meniscal replacement, or prosthesis, which does not interfere with normal joint motion, which would lead to either a reduced range of motion, or focal concentration of force at other sites within the joint and therefore progressive cartilage destruction.

Yet another object is to provide a meniscal replacement or prosthesis which is biomechanically able to withstand normal joint forces and is able to function at those loads to protect the cartilage and stabilize the joint.

Still another object is to provide a meniscal replacement or prosthesis which acts as a scaffold for meniscal fibrochondrocyte infiltration, and which is subsequently replaced.

A further object is to provide a meniscal replacement or prosthesis which is composed of biocompatable materials having an organization equivalent to that of the normal meniscus; thereby not evoking an immunologic reaction, nor aggravating other joint structures.

Still a further object is to provide a meniscal replacement or prosthesis which is adapted for implantation by standard operative techniques, preferably transarthroscopically.

SUMMARY OF THE INVENTION

The present invention provides a structure for implantation into the knee joint which assumes the form and role of a meniscus. This prosthetic meniscus may also promote regrowth of meniscal tissue and may provide a scaffold for the regenerating tissue.

The prosthetic meniscus is generally a three dimensional array of collagen fibers interspersed and crosslinked with glycosaminoglycan molecules. The array may have a simple crescent-shaped wedge, cylindrical pad, or other shape. The structure comprises about 65–95% Type I collagen and about 1–25% glycosaminoglycans by dry weight, the proportions of which may be constant throughout the structure or may be variable.

In the structure, the collagen fibers may be randomly orientated throughout the structure, or ordered at specified regions. Alternatively, the fibers may assume substantially circumferential and radial orientations at specified regions of the structure or may be found uniformly throughout the prosthetic meniscus.

The glycosaminoglycans (GAGs) consist of at least one of the group of molecules comprising chondroitin 4-sulfate; chondroitin 6-sulfate; keratin sulfate; dermatan sulfate; and hyaluronic acid. These GAGs may be uniformly dispersed throughout the prosthetic meniscus as individual molecules, or may be present in differing amounts in different regions of the structure.

However, at least a portion of the GAG molecules comprising the prosthetic meniscus are constituents of chemical crosslinks which bridge neighboring collagen fibers. These crosslinks are composed of at least one polymerized GAG molecule, and have a molecular weight in the range 800–60,000 daltons.

In various forms of the invention, GAG crosslinks may be uniformly dispersed throughout the prosthetic meniscus at a density of less than about 0.9 but greater than about 0.5, as expressed by the 3-hydroxypyridium crosslink/collagen molar ratio, thereby permitting the ingrowth of regenerating meniscal tissue, and eventually providing a fluidic impedance similar to that of normal meniscus of about $1/8.13 \times 10^{-16}$ m$^4$/N.s. In other forms of the invention, the density of these crosslinks may be greater than about 0.9, providing a fluidic impedance of greater than about $1/8.13 \times 10^{-16}$ m$^4$/N.s, and thereby being dense enough to act as a protective and lubricating barrier between the femur and tibia. These crosslinks may also be located with varying densities a specified regions of the prosthetic meniscus, permitting greater physical strength at anticipated high stress points.

In accordance with another aspect of the invention, the prosthetic meniscus may further comprise a mesh composed of a dissolvable, nonimmunogenic material which is attached to portions of the outer surface of the prosthetic meniscus. The mesh, which may be in the form of suture material, aids in the successful implantation of the prosthetic meniscus into the knee joint by providing a temporary anchoring mechanism.

BRIEF DESCRIPTION OF THE DRAWINGS

The foregoing and other objects of this invention, the various features thereof, as well as the invention, itself, may be more fully understood from the following description, when read together with the accompanying drawings.

DESCRIPTION OF THE PREFERRED EMBODIMENT

Figure 1:
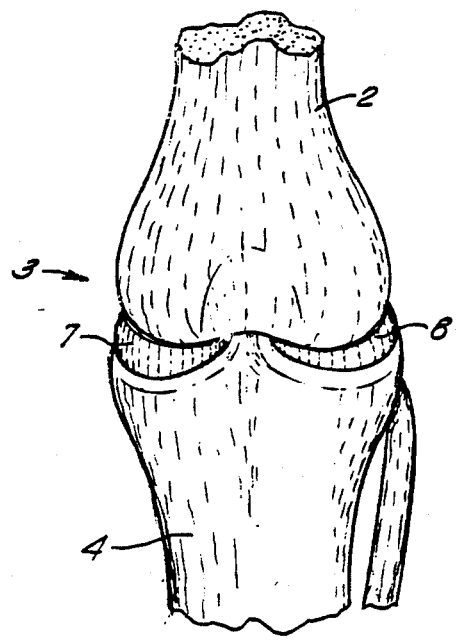
FIG. 1 shows a simplified, diagramatic representation of a humanoid knee joint, with menisci in native positioning.

FIG. 1 shows a diagramatic representation of the normal postioning of medial meniscus 7 and collateral meniscus 8 in the human knee joint 3 between the femur 2 and tibia 4.

Figure 3:
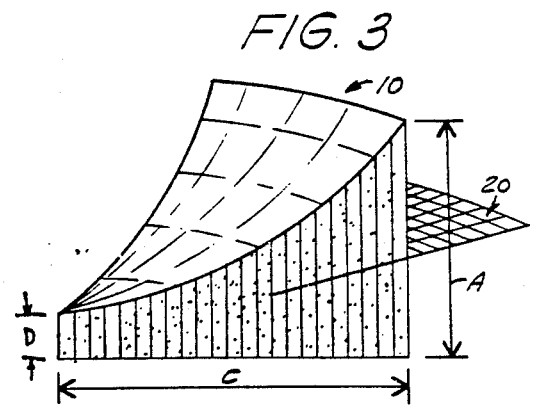
FIG. 3 shows a perspective radial section of the prosthetic meniscus of FIG. 2.
Figure 2:
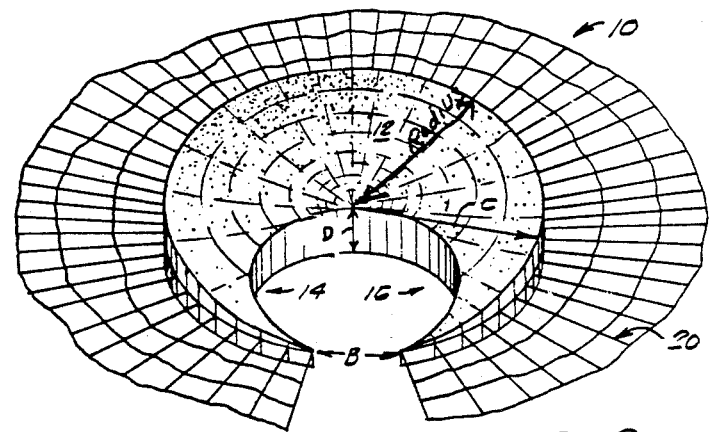
FIG. 2 shows a perspective view of an exemplary prosthetic meniscus in accordance with the present invention.

FIGS. 2 and 3 show an exemplary prosthetic meniscus 10 embodying the present invention. The prosthetic meniscus 10 is adapted for implantation in the normal location in the knee joint.

Generally, the prosthetic meniscus 10 has the shape of a crescent-shaped wedge comprising a relatively wide central region 12 between two narrow distal regions 14 and 16. In the preferred form, the wedge has height A at its peripheral edge of approximately 0.4 inches, a height D at its central point of approximately 0.2 inches, and a radius C of approximately 1.0 inches. The crescent shaped wedge subtends an angle B substantially in the range of about 25 to about 45 degrees, and preferably of about 30 degrees.

The prosthetic meniscus is composed essentially of collagen and glycosaminoglycans (GAGs), and more particularly, of a three-dimensional array of collagen type I fibers interconnected via crosslinks consisting of polymerized GAG molecules. In other embodiments, additional GAG molecules may be present outside of the crosslinked GAGs.

In the preferred embodiment, the collagen fibers in the array are ordered in substantially circumferentially-extending and substantially radially-extending orientations, with the density of fibers being substantially uniform throughout the array. However, in other embodiments, the array of collagen fibers may be unordered. In either configuration, ordered or unordered, the density of said fibers may be non-uniform, particularly having high densities at points in the prosthetic meniscus at which high stress levels are anticipated, such as at the distal regions 14 and 16.

The GAG crosslinks have a molecular weight in the range of 600 to 80,000 daltons, and are composed typically of at least one of the group of GAG molecules consisting of chondroitin 4-sulfate; chondroitin 6-sulfate; keratin sulfate; dermatan sulfate; and hyaluronic acid. The dispersion of GAG crosslinks is preferably uniform, but may be more concentrated at anticipated points of high stress, typically at the distal regions 14 and 16, and less concentrated in the central region 12. In such configurations, the GAG concentration may be in the range of about 3–25% in the distal regions 14 and 16, and in the range of about 1–10% in the central region 12. However, when uniform, the dispersion of GAG crosslinks throughout the prosthetic meniscus may be, for example, in the range of about 1–15%.

In the preferred embodiment, the density of the crosslinks is relatively low (for example, on the order of about 0.7 crosslink/collagen molar ratio) in the array to permit ingrowth of regenerated meniscal tissue. In other embodiments, the density of said crosslinks may be relatively high (for example, on the order of 0.9 crosslink/collagen ration) to provide cushioning, lubrication and support for the knee joint and to slow vascular ingrowth, thereby diminishing the rate of scaffold resorption.

In the embodiment illustrated in FIG. 2, the prosthetic meniscus 10 includes a mesh member 20 extending from its peripheral edge. The mesh member 20 is composed of a nonantigenic, dissolvable suture material, and provides a readily used means for anchoring the meniscus 10 in place. The mesh member 20 may function in this capacity until sufficient tissue ingrowth occurs to then provide that function. By way of an example, the mesh member 20 may be a #1 mesh screen composed of absorbable suture materials such as polyglyconate, Dexon or polydioxane (PDS) woven into a mesh. Nonabsorbable suture materials such as Gore-tex may also be used.

Figure 4:
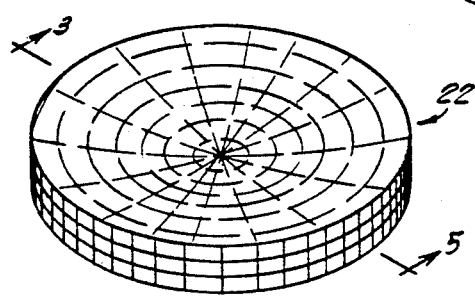
FIG. 4 shows a perspective view of an alternative embodiment of the present invention.
Figure 5:
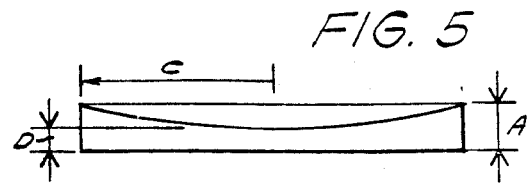
FIG. 5 shows a sectional view along line 5—5 of the prosthetic meniscus of FIG. 4.

FIGS. 4 and 5 show additional embodiments of the present invention which are similar in composition to the prosthetic meniscus depicted in FIG. 2. More particularly, FIG. 4 depicts a right circular cylinder-shaped meniscus 22. FIG. 5 shows a sectional view along line 5—5 of the meniscus shown in FIG. 4.

In other forms of the invention, still other shapes may be used, particularly with varying densities of collagen fibers and dispersions of GAG molecules and crosslinks, permitting accommodation of differing stress levels, rates of ingrowth, and resiliency.

Exemplary menisci may be constructed in the following manner:

EXAMPLE I (A) Type I collagen from bovine Achilles tendon is mechanically processed to disintegrated tissue, soaked in 0.1% N HCl, and mechanically compressed under high pressure while methodically narrowing the gap between metal rollers. Swollen collagen fibers are dehydrated in 20% NaCl for 3 days, and the mechanical separation repeated. Final mechanical separation is repeated at pH 3.0–3.5 in the presence of 0.7% NaCl. The deswollen fibers produce 20 to 30 centimeter long fibers at pH 3.0–3.5. These fibers are ground into a dispersion and further washed in 0.7% NaCl and neutralized in the presence of 0.1% HCl as described above. They are then suspended in a 20% NaCl solution. Ethanol may be added to decrease the isoelectric point and further increase the concentration of collagen fibers in the dispersion.

(B) The fiber dispersion is then subjected to dehydrothermal crosslinking conditions: heating to from about 100 to 135 degrees C. for about 24 to 72 hours, and then further crosslinked by exposure for 1–15 hours to 0.1–0.5% glutaraldehyde at room temperature.

(C) Further neutralization and washes with a balanced electrolyte solution containing 20% NACl and 25% acetone in 0.5M phosphate buffer, pH 5.5 are carried out. Multiple washes in the buffered salt-acetone solution also containing 0.5M EDTA are also performed. The final rinse step includes 0.15M phosphate buffer, 7.2, with drying in preformed meniscal molds.

EXAMPLE II (A)–(C) same as steps (A)–(C) described in EXAMPLE I.

(D) While in dispersion form, selected glycosaminoglycans are added which may include chondroitin 6-sulfate, chondroitin 4-sulfate, hyaluronate, dermatan sulfate, and keratin sulfate to a concentration of about 0.5–25 weight %, preferably to about 2.5 weight %. The GAGs are allowed to diffuse freely in the solution, creating a porous matrix with properties defined by the pore sizes of 30–60 microns, the purity of the collagen at 99.9%, the density of the structure, and the quantity of GAGS.

EXAMPLE III (A)–(D) same as steps (A)–(D) as described in Example II.

(E) For attachment purposes, a mesh of absorbable polyglyconate suture material, matched to the size of the mold, is laid in the dispersed collagen such that it protrudes from the structure's periphery to form a skirt which may extend over the tibial plateau. This mesh provides both immediate attachment sites and long term fibrous ingrowth.

EXAMPLE IV (A)–(C) same as steps (A)–(C) as described in EXAMPLES I and II.

(D*) While in dispersion form, selected glycosaminoglycans are added. The dispersion is then subjected to pressurization to 20,000 lbs compressing the structure to reduce the pore sizes to 10–50 microns.

(E) same as step (E) as described in EXAMPLE III.

EXAMPLE V (A) same as step (A) as described in EXAMPLES I–IV.

(B) The fiber dispersion is then crosslinked by exposure for 1–15 hours to 0.05M 1-ethyl-3-(3-dimethylaminopropyl) carbodiimide-HCl in a balanced electrolyte solution at pH 5.0 at room temperature.

(C) same as step (C) as described in EXAMPLES I–IV.

(D) same as step (D) as described in EXAMPLES II and III.

EXAMPLE VI (A) same as step (A) as described in EXAMPLES I–V.

(B) The fiber dispersion is then subjected to dehydrothermal crosslinking conditions: heating to from about 100 to 135 degrees C. for about 24 to 72 hours, and then further crosslinked by exposure for 1–15 hours to 0.05M 1-ethyl-3-(3-dimethylaminopropyl) carbodiimide-HCl in a balanced electrolyte solution, pH 5.0 at room temperature.

Other chemical crosslinking reagents known to those skilled in the art (such as hexamethylene diisocyanate) may be substituted for glutaraldehyde or carbodiimide in the above EXAMPLES.

With the processes described in the above examples, a prosthetic meniscus of the form shown in FIGS. 2 and 3 may be constructed having the following dimensions:
height A=0.20–0.40 inches
angle B=25°–45° degrees
radius C=0.5–2.0 inches
height D=0.05–0.1 inches Generally, that exemplary meniscus has substantially uniform GAG concentration of approximately 50 mg/ml of tissue, and crosslink density as expressed by the 3-hydroxy pyridinium crosslink/collagen molar ratio of 0.86 when the collagen has a content of >85% by dry weight. In the preferred form, the functional characteristics of the exemplary meniscus after repopulation with host meniscal fibrochondrocytes are as set forth in Table 1.

TABLE 1

| | |
|---|---|
| Physiologic Loading Rate: | 70–100 kg/cm$^2$/sec |
| Strain Rate: | 1.7–9%/sec |
| Breaking Strain: | 15–25% |
| Modulus of Elasticity: (of hydrated tissue after creep) | 0.412 mPa |
| Modulus of Superficial (200 um) Isotropic Fibers: | 45–65 mPa |
| Modulus of Deep Anisotropic Fibers: | |
| Circumferential Fibers: | |
| Superficial | 35–55 mPa |

TABLE 1-continued

| | |
|---|---|
| Middle | 185–205 mPa |
| Deep | 130–150 mPa |
| Radial Fibers: | |
| Superficial | 65–80 mPa |
| Middle | 1–4 mPa |
| Deep | 3–6 mPa |
| Average Permeability Density Coefficient: | $8.13 \times 10^{-16}$ m$^4$/N.s. |
| Coefficient of Friction | 0.001 when covered in synovial fluid |

The invention may be embodied with other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A prosthetic meniscus comprising a porous dry volume matrix of Type I collagen fibers interspersed with glycosaminoglycan molecules, wherein said matrix has a substantially wedge shape including a wide central region between two narrow distal tip regions, wherein said collagen fibers are present at a concentration of about 65%–98% by dry weight, wherein said glycosaminoglycan molecules are present at a concentration of about 1%–25% by dry weight, and wherein at least a portion of said molecules provide glycosaminoglycan crosslinks between said collagen fibers, said crosslinks being dispersed substantially nonuniformly throughout said matrix, and said crosslinks having relatively high density at said tip regions and relatively low density at said central region, and wherein said matrix has a pore size substantially in the range 10–50 microns, whereby said matrix establishes an at least partially bioresorbable scaffold adapted for ingrowth of meniscal fibrochondrocytes.

2. The prosthetic meniscus of claim 1, wherein said glycosaminoglycan molecules consist of at least one of the group comprising:chondroitin 4-sulfate; chondroitin 6-sulfate; keratin sulfate; dermatan sulfate; and hyaluronic acid.

3. The prosthetic meniscus of claim 2, wherein the dispersion of said glycosaminoglycan molecules is substantially uniform throughout said matrix.

4. The prosthetic meniscus of claim 2, wherein the dispersion of said glycosaminoglycan molecules is substantially non-uniform throughout said matrix.

5. The prosthetic meniscus of claim 1, wherein said crosslinks consists of at least one of the group of glycosaminoglycan molecules comprising: chondroitin 4-sulfate; chondroitin 6-sulfate; keratin sulfate; dermatan sulfate; and hyaluronic acid, and wherein the molecular weight of said molecular crosslinks is within the range of 800–60,000 daltons.

6. The prosthetic meniscus of claim 5 wherein the density of said collagen fibers is substantially uniform throughout said matrix.

7. The prosthetic meniscus of claim 1, wherein the orientation of said collagen fibers is substantially random throughout said meniscus.

8. The prosthetic meniscus of claim 1, wherein the density of said collagen fibers is substantially non-uniform throughout said array.

9. The prosthetic meniscus of claim 1, further comprising a mesh extending from portions of the outer surface of said matrix, said mesh being dissolvable and nonimmunogenic.

10. The prosthetic meniscus of claim 1, wherein said glycosaminoglycan crosslinks comprises at least one of the group of glycosaminoglycan molecules consisting of:chondroitin 4-sulfate; chondroitin 6-sulfate; keratin sulfate; dermatan sulfate; and hyaluronic acid, and wherein the molecular weight of said molecular crosslinks is within the range of about 800–60,000 daltons.

11. The prosthetic meniscus of claim 10, wherein said glycosaminoglycan crosslinks are present at a density less than about 0.95 and greater than about 0.50 crosslink/collagen ratio, thereby permitting ingrowth of, and providing support for regenerated meniscal tissue.

12. The prosthetic meniscus of claim 10, further comprising a mesh extending from portions of the outer surface of said array, said mesh being absorbable and nonimmunogenic.

* * * * *